United States Patent [19]

Green et al.

[11] 4,086,926
[45] May 2, 1978

[54] LIGATING AND DIVIDING ORGANIC STRUCTURES

[75] Inventors: David Thomas Green; Richard A. McGarry, both of Norwalk, Conn.

[73] Assignee: United States Surgical Corporation, New York, N.Y.

[21] Appl. No.: 730,821

[22] Filed: Oct. 8, 1976

[51] Int. Cl.² ............................................. A61B 17/11
[52] U.S. Cl. ................................ 128/334 R; 128/305
[58] Field of Search ........................... 128/305, 334 R

[56] References Cited
U.S. PATENT DOCUMENTS

| 3,545,444 | 12/1970 | Green | 128/305 |
| 3,584,628 | 6/1971 | Green | 128/305 |
| 3,665,924 | 5/1972 | Nolles et al. | 128/305 |
| 3,683,927 | 8/1972 | Noiles | 128/305 |
| 3,740,994 | 6/1973 | DeCarlo, Jr. | 72/407 |
| 3,955,581 | 5/1976 | Spasiano et al. | 128/334 R |

Primary Examiner—Robert W. Michell
Assistant Examiner—Michael H. Thaler
Attorney, Agent, or Firm—Fleit & Jacobson

[57] ABSTRACT

A cartridge is provided for ligating and dividing organic structures such as blood vessels or a band of tissue containing a plurality of blood vessels, nerves or the like. The cartridge operates in three stages and is adapted to associate with an instrument which provides power to the cartridge. After the structure is inserted between the jaws of the cartridge, the cartridge jaws close, a pair of pushers moves forward and ligates the structure at two spaced apart locations with a pair of surgical staples, and a knife then comes forward and divides the ligated structure at a position intermediate the pair of staples. The staple feeding arrangement comprises a pair of belts advanced by the pushers, the belts each carrying a plurality of staples. The staples are transferred from the plane of the belts to the plane of the pushers by ramp surfaces. The belts are kept from backing up during the return stroke of the pushers by a pair of detents associated with the belts. The knife is associated with the main body of the cartridge by means of a novel shifter mechanism in such a manner that the initial movement of the knife causes the jaws of the cartridge to close. A mechanism is provided to prevent the knife from severing the ligated structure in the event, for example, that all of the staples have been expelled from the cartridge. Finally, a cartridge lock mechanism maintains the operative elements of the cartridge in proper position until the cartridge is mounted on the instrument.

28 Claims, 15 Drawing Figures

LIGATING AND DIVIDING ORGANIC STRUCTURES

BACKGROUND OF THE INVENTION

In commonly assigned U.S. Pat. Nos. 3,665,924 and 3,740,994, a novel cartridge and instrument for ligating and dividing organic structures by means of surgical staples are disclosed. The present invention relates to a cartridge which, together with an instrument such as disclosed in the commonly assigned patents, is similarly capable of mechanically and repetitiously ligating and dividing organic structures, such as blood vessels and the like.

The cartridge of the present invention is adapted to operate in three stages such as disclosed in the commonly assigned patents. Once the organic structure is inserted within the area of its jaws, the main body and wrap of the cartridge are moved forward toward an anvil member fixed relative to the instrument, thereby enclosing the structure within the jaws of the cartridge. Then a pair of pusher elements is advanced and moves a pair of staples toward the anvil assembly. During the forward portion of the pusher stroke, the respective staples encircle the structure at spaced locations and are crimped about the structure in such a manner that the structure is sealed at two locations. Finally, and with the pushers at the forwardmost portions of their strokes, a knife blade advances and divides the structure intermediate the two staples. The staple closure and crimping sequence is disclosed in commonly assigned U.S. Pat. No. 3,683,927.

The instrument disclosed in the commonly assigned patents is of three stage-design. The forward end of the instrument is provided with three saddles which associate, respectively, with the cartridge wrap, the pushers and the knife of the three-stage cartridge disclosed therein. Three spring elements are housed in the instruments and, in conjunction with a trigger element, operate the cartridge wrap, the pushers and the knife through the three saddle elements. With a cartridge mounted on the instrument, the initial squeezing of the handle moves the cartridge wrap toward the fixed anvil assemblies, and the further squeezing overcomes the force exerted by one of the springs and advances the pushers toward the respective anvils and ultimately, after overcoming the force exerted by another of the springs, urges the knife toward the front of the instrument to effect a severing operation.

In commonly assigned U.S. Pat. No. 3,955,581, a three-stage instrument is also disclosed for operating a cartridge by means of three saddle elements. One of the saddle elements, controlling the pusher, is in direct mechanical association with a trigger operable by the surgeon. One of the remaining saddle elements, controlling the closing of the jaws, is operable in response to the position of the trigger-controlled saddle element through the means of a novel shifter dog arrangement. The third saddle element, controlling the knife of the cartridge, is actuated by a linkage whose operation is controlled directly by the trigger. In this manner, the drawbacks associated with the multiple biasing springs in commonly assigned U.S. Pat. Nos. 3,665,924 and 3,740,994 are avoided.

Although these prior art instruments and cartridge have proved satisfactory in practice, there are certain disadvantages associated with the cartridge. First, because of the cartridge design, the instrument is required to have a three-stage operation. This makes the instrument more complicated to design and engineer and to manufacture. Moreover, the cartridge is designed to advance the staples and transfer them out of the index plane into the plane of the pushers by means of a complex staple feeding arrangement which takes the form of a pair of interacting leaf spring assemblies. This in turn requires close tolerances to be maintained in the manufacture of the cartridge. Also, the cartridge does not have means for locking the cartridge components in position during shipment and prior to mounting the cartridge on the instrument (or means for preventing the inadvertent actuation of the knife after, for example, all of the staples have been expelled from the cartridge) which is as easy to engineer and manufacture as is desired.

Accordingly, it is a broad object of this invention to provide a new cartridge design for ligating and dividing an organic structure.

It is another object of this invention to provide a new cartridge design which will ligate and divide organic structures by means of association with a two-stage instrument.

It is still another object of this invention to provide a new cartridge design in which the associated instrument powers the knife and pushers and the knife is so associated with the main body portions and wraps of the cartridge that the jaws of the cartridge are closed and opened as the knife is moved forward and backward.

It is yet another object of this invention to provide a new cartridge design which has improved means for advancing, forming, and ejecting the staples.

Another object of this invention is to provide a new cartridge design which has improved means for advancing the staples toward the anvil assembly in readiness for ejection.

Still another object of this invention is to provide a new cartridge design which has improved means for locking the cartridge during shipment and preventing the inadvertent severing of organic structures when all of the staples, for example, have been expelled from the cartridge.

These and other objects of the invention, as well as many of the attendant advantages thereof, will become more readily apparent when reference is made to the following description taken in conjunction with the drawings.

SUMMARY OF THE INVENTION

The present invention relates to a three-stage cartridge for associating with an instrument and adapted to ligate and divide organic structures. The cartridge is simple, and yet effective, and eliminates numerous disadvantages common in prior art cartridges.

The cartridge operates in three stages. Once a tubular structure is inserted within the area of the cartridge jaws, the cartridge main body portions and associated wraps move forward toward an anvil assembly integral with a rail assembly fixed on the instrument, thereby enclosing the structure within the jaws of the cartridge. Then, a pair of pusher elements is advanced and moves a pair of staples toward the anvil assembly. At the forward portions of the pusher strokes, the respective staples encircle the tubular structure at spaced locations and are subsequently crimped about the structure in such a manner that the structure is sealed at two locations. Finally, and with the pushers at the forwardmost portions of their strokes, a knife blade advances and divides the tubular structure intermediate the two staples.

The cartridge houses a plurality of the staples mounted on a belt so that the staple arms overlap in a "shingle" arrangement. The pushers slidably mounted in the cartridge advance the belts and move the forwardmost staples up a series of ramps out of the plane of the belt and into the major planes of the pushers and then push and form the staples against the anvil assembly. As the forwardmost pair of staples is being advanced, they are held in the teeth in the belt by leaf springs associated with the wraps. On the return stroke of the pushers, a pair of detents associated with the main body portions of the cartridge prevent the belts and staples from moving rearward from the anvil assembly. A fail-safe mechanism is provided to stop the forward movement of the pushers and thereby prevent the knife from severing an organic structure in the jaws of the cartridge in the event that two staples have not been advanced by the pushers as, for instance, when all of the staples have been expelled from the cartridge. A locking mechanism is provided to keep the respective components of the cartridge in proper position to be associated with the instrument and to prevent the accidental ejection of staples from the cartridge and the actuation of the knife before association with the instrument. Also, an ejector mechanism is provided in order to force the formed staples out of the jaws of the cartridge once the organic structure has been ligated and divided.

The operation of the cartridge of the invention is controlled through the means of two saddle elements of an associated instrument. One of the saddle elements controls the pushers and the other saddle element controls the knife. Because of the design of the cartridge, the remaining saddle element which was used in the prior instrument designs for controlling the wrap or main body portion to open and close the jaws of the cartridge is no longer required. Rather, the cartridge contains a shifter mechanism which is associated with the knife and the main body portions and associated wraps.

As the knife is initially moved forward by the instrument, the jaws of the cartridge are closed. Conversely, the return stroke of the knife also caused by the instrument, open the jaws. Accordingly, in view of the new cartridge design, if the cartridge is associated with an instrument such as disclosed in commonly assigned U.S. Pat. Nos. 3,665,924 and 3,740,994, or with an instrument such as disclosed in commonly assigned U.S. Pat. No. 3,955,581, the saddle (30 and 24, respectively) designed to be associated with the main body portion or wrap performs no function and may be omitted along with the associated apparatus for controlling and moving the saddle.

DESCRIPTION OF THE PREFERRED EMBODIMENT

Referring first particularly to FIGS. 1-5, the cartridge 10 comprises a rail assembly 12 adapted to be fixedly secured to the instrument 14 by means of shank 15 of rail assembly 12, the projections 16 on the shank 15 and the thumb operated lock (not shown) on the instrument. A curved anvil assembly 20 comprising a pair of spaced apart anvils 22 and 24 is integral with and defined by the forward end of the rail assembly 12. A pair of main body portions 26 are slidably mounted on the rail assembly 12, and a pair of wraps 28 are fixedly secured to and moveable with the respective main body portions 26 by a pair of bands 30. A pair of pusher elements 32 is slidably mounted between the main body portions 26 and the respective wraps 28. A knife 34, centrally located in the cartridge 10, is slidably mounted between the respective wraps 28. As can be seen best in FIGS. 6 and 10, the saddles 36 and 38 associate with and control the movements of the knife 34 and the pushers 32, respectively, with respect to the rail assembly 12. As will be described in more detail below, the knife 34 is operatively associated with the wraps 28 by means of a novel shifter dog in such a manner that the movements of the wraps 28 and the main body portions 26 are controlled by the movement of the knife 34. For simplicity of description, only one side of the cartridge will be described, but it should be understood that the cartridge is symmetrical about its longitudinal centerline.

With reference now particularly to FIGS. 2, 4, 10, and 11, the cartridge 10 is provided with a staple feeding arrangement comprising a belt 40, made of flexible plastic, mounted between the guide rails 42 defined by the main body portion 26 to form a loop which passes through the belt openings 44 and 46 near each longitudinal end of the main body portion. The ends of the belt 40 are connected together by a spring 48. The belt 40 has a plurality of longitudinally spaced apart pairs of teeth 50 on one side thereof. Between each pair of teeth is defined a staple-carrying groove 52. Openings 54 are provided in the belt 40 between each adjacent pair of teeth 50. A detent 60 is provided in an opening 62 in the forward portion of the side wall 63 of the main body portion 26. The detent 60 is aligned with the openings 54 in the belt 40 and is resiliently biased into the plane of the belt 40 to prevent the belt from backing up during the return stroke of the pusher. The detent 60 has a sloped rear surface 60', however, to permit the detent to be cammed out of the plane of the belt 40 when the belt is being advanced. A cover plate 68 is fitted into a slot 70 in the outer surface of the side wall 64 of the main body portion 26. The cover plate 68 has indicia 72 thereon which, in association with a reference mark 74 on the spring 48, may be used to determine the number of pairs of staples remaining in the cartridge.

Figure 8:
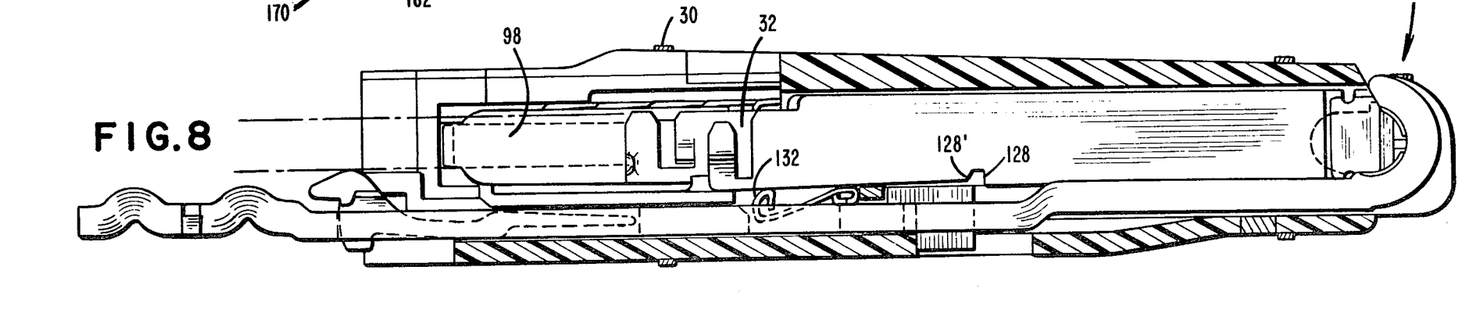
Figures 9, 10:
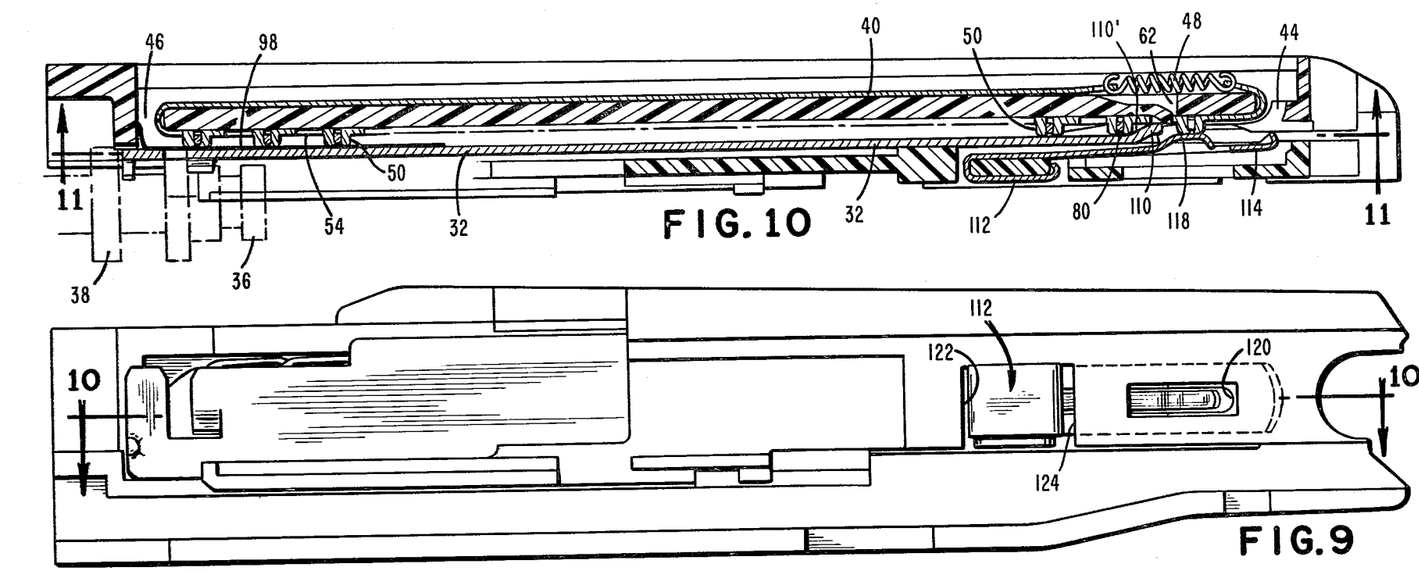
FIG. 9 is a side view of the cartridge showing one of the main body portions and associated wraps and one of the pushers.
FIG. 10 is a cross-sectional view taken along the lines 10—10 in FIG. 9 and showing the association of the cartridge with the drive means of a surgical instrument shown in phantom lines.
Figure 11:
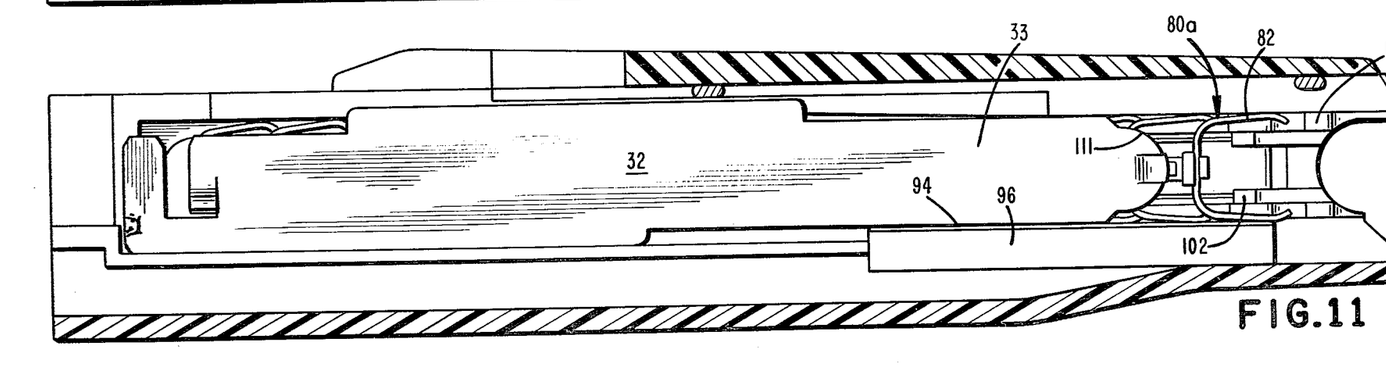

As shown particularly in FIGS. 10 and 11, the staples 80 are housed in and guided by the staple-carrying grooves 52 of the belt 40. The staples 80, as mounted in the belt, have a pair of arms 82 terminating in widely spaced apart ends 84 which extend in the longitudinal direction of the main body portion 26 of the cartridge. The staples 80 also have cross-pieces 86 which extend transversely of the arms 82 and the belt 40. The cross-pieces 86 of the staples 80 are fitted into the staple-carrying grooves 52. The staples 80 are mounted on the belt 40 so that the ends 84 of the staples lie in a pair of grooves 90 defined in the main body portion 26 on both sides of the guide rails 42. The forward lower wall of the lower one of the grooves 90 is formed by the leg 94 of a "L" shaped member 96 fitted into the main body portion 26. The ends 84 of each of the staples 80, with the exception of the forwardmost staple, rests under the arms 82 of the preceding staple in "shingle" fashion. The rear portion of the belt 40 is covered by a cover strap 98 shown particularly in FIG. 8 positioned between the belt and the pusher 32 to keep the rear end of the pusher from interfering with the movement of the belt or staples during the advance and retraction of the pusher.

The staples 80 lie along the major portion of the length of the cartridge 10 in what may be termed an index plane. It is in the index plane that the staples are, in unison, advanced toward the anvil assembly 20 in readiness for ejection. Near the forward end of the cartridge 10, the staples 80 are transferred to the pusher plane coincident with the plane of the major portion of the pusher 32. For purposes of transferring the staples 80 from the index plane to the pusher plane, the main body portion 26 is provided with a first pair of ramps 100 which are spaced apart to act on the individual staples at their respective ends 84 and a second pair of ramps 102 which are spaced apart to act on the individual staples at their respective cross-pieces 86.

Figure 3:
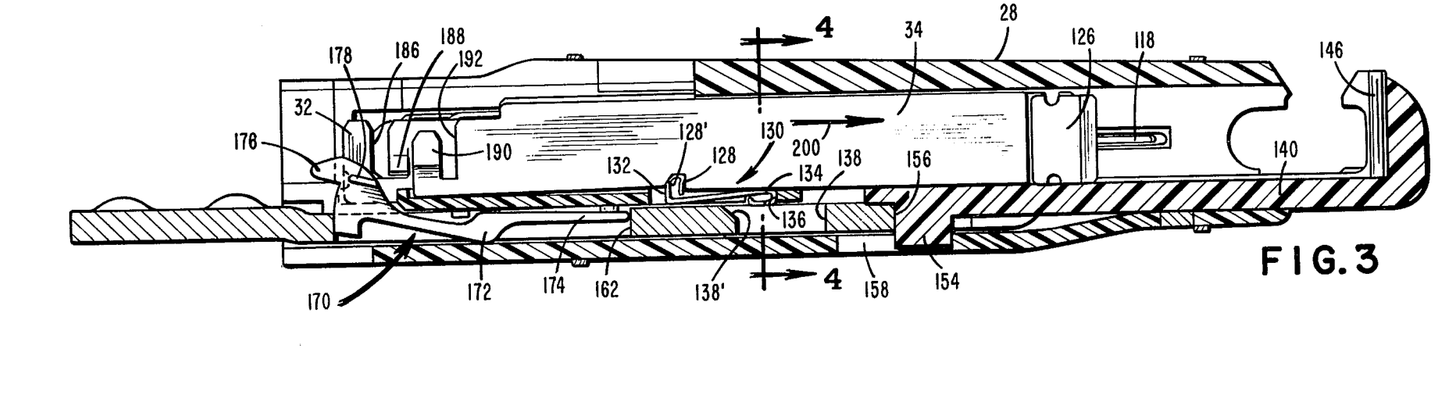
FIG. 3 is a cross-sectional view of the cartridge taken along the lines 3—3 in FIG. 1.
Figure 4:
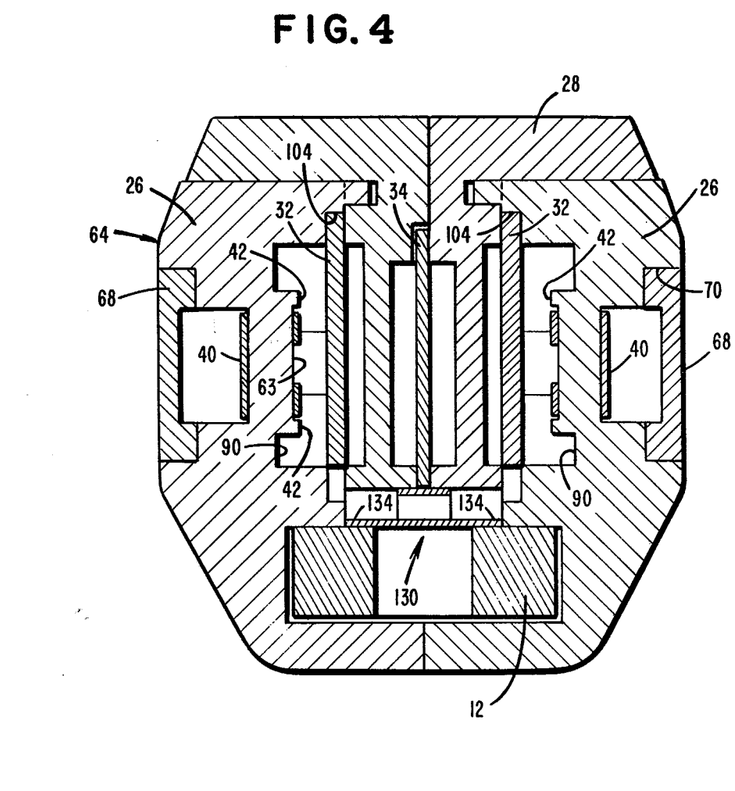
FIG. 4 is a cross-sectional view of the cartridge taken along the lines 4—4 in FIG. 3.

Referring now particularly to FIGS. 3, 4, 10, 11 and 12, the pusher 32 slides along ledges 104 defined by the main body portion 26 and the wrap 28 as shown particularly in FIG. 4. The pusher 32 is positioned adjacent the belt 40 and the staples 80 and is adapted for movement longitudinally within the cartridge 10. As best seen in FIG. 10, while the major part of the pusher 32 lies in the pusher plane, a tooth 110 at the forward end of the pusher 32 projects into the index plane and, more specifically, into the plane of the belt teeth. The tooth 110 is centered on the belt 40 and is adapted to associate with the pairs of teeth 50 of the belt as shown particularly in FIG. 12. The rear surface 110' of the tooth 110 is sloped to allow the front of the pusher 32 to be cammed out of the index plane by the belt 40 during its return stroke. Forward portion 33 of pusher 32 flexes inwardly during this camming action. The forward end 111 of the pusher 32 is curved as shown particularly in FIG. 11 and is adapted to cooperate with the individual staples 80 during the staple forming operation.

Figure 14:
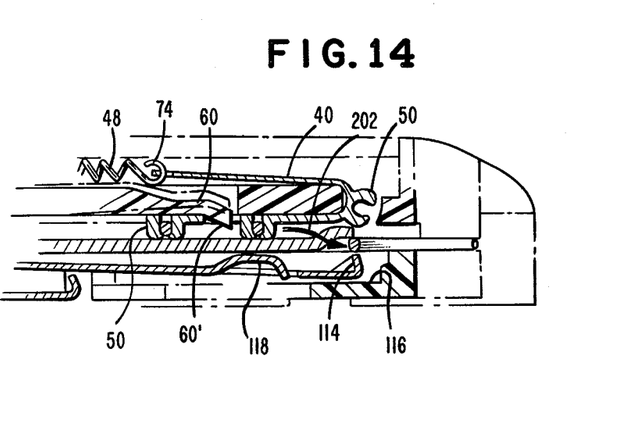

With reference now particularly to FIGS. 9, 10, 12 and 14, a spring 112 is attached to the forward end of the wrap 28. This spring 112 extends longitudinally of the cartridge 10 and is primarily positioned between the wrap 28 and the pusher 32. The forward end of the spring 112 comprises a lip 114 which has a curvature corresponding to the curvature of the forward end of the pusher 32. The lip 114 is cammed out of the pusher plane into a slot 116 in the wrap 28 by the individual staples during the staple forming operation as shown in FIG. 14. However, when the cartridge 10 is empty, the lip 114 remains in the pusher plane and prevents the pusher 32 from advancing. In this manner, and as will be discussed in more detail below, the knife 34 is also prevented from advancing and severing an organic structure enclosed in the jaws of the cartridge 10 when there are not two staples in the cartridge in front of the pushers to ligate the structure.

Figure 12:
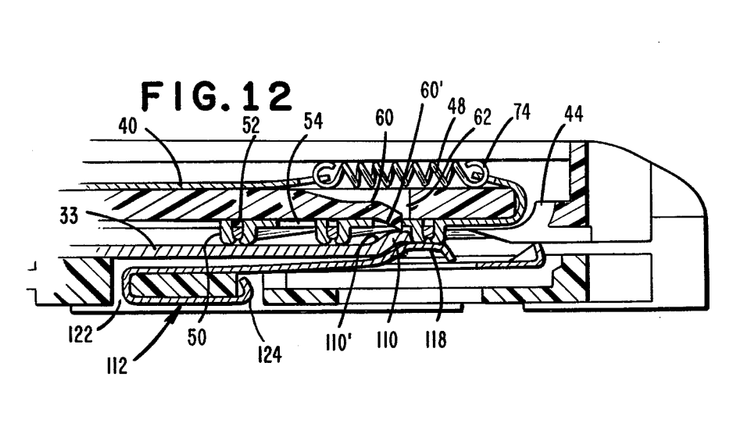
FIGS. 12 and 14 are enlarged views of the forward end of the cartridge as shown in FIG. 10 showing the advance of one of the pushers and one of the belts and the transfer of one of the forwardmost staples into the plane of the pusher.

The spring 112 also has a leaf spring 118 located in an elongated opening 120 in the spring 112 which projects into the index plane and, more specifically, into the plane of the belt teeth 50 as shown in FIGS. 10 and 12. The function of the leaf spring 118 is to hold the forwardmost staple in the belt 40 in the staple-carrying groove 52 defined by the pair of teeth 50 carrying this staple until the staple is ready to be transferred out of the index plane into the pusher plane. As this occurs, the leaf spring 118 is cammed into the slot 116 in the wrap 26 by the pusher 32 as shown in FIG. 14. The rear portion of the spring 112 extends through opening 122 and into opening 124 in the wrap 28 in order to securely mount the spring to the wrap.

Figure 6:
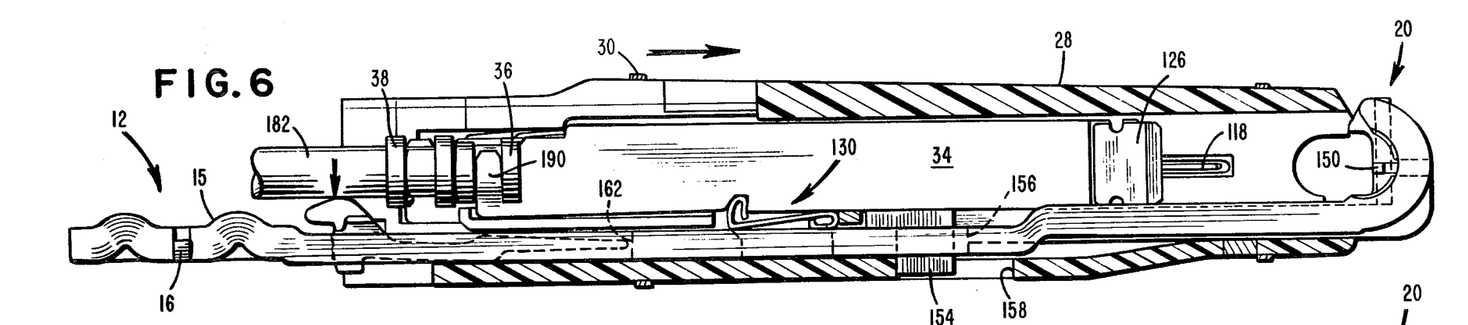
FIGS. 6-8 are a series of three cross-sectional views of the cartridge taken along the lines 3—3 in FIG. 1 showing the movements of one of the main body portions and associated wraps, one of the pushers, the knife and the shifter dog as the jaws of the cartridge are closed and the pushers and knife advance as well as the association of the cartridge with the drive means of a surgical instrument.
Figure 7:
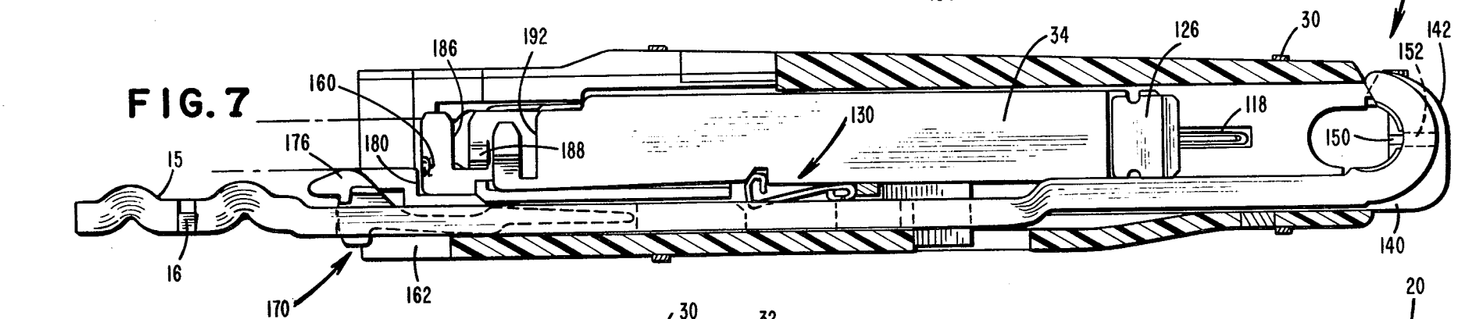

Referring now particularly to FIGS. 3, 4 and 6-8, the knife 34, which has a blade 126 mounted on its forward end, slides between the wraps 28 of the cartridge 10. The knife has a notch 128 formed in its bottom surface intermediate its ends which is adapted to associate with a shifter dog 130. The shifter dog 130 has an upstanding arcuate portion 132 at its rear end for fitting into the notch 128 in the knife 34. At its forward end, the shifter dog 130 has two outwardly and downwardly extending projections 134 which fit into and are hingedly secured in slots 136 formed in the wraps 28. A longitudinally extending opening 138 is formed in the rail assembly 12 which has a sloped portion 138' at its rear end. The shifter dog 130 rides along the upper surface of the rail assembly 12 with its upstanding arcuate portion 132 locked in the notch 128 in the knife 34 as shown in FIG. 3 until the main body portion 26 and associated wrap 28 are abutting against the anvil assembly 20 thus closing the jaws of the cartridge around the organic structure as shown in FIG. 6. Then, the rear end of the shifter mechanism 130 is cammed into slot 138 in the rail assembly by the sloped rear portion 128' of the notch 128 as shown in FIGS. 7 and 8 so that the knife can continue its advance to divide the ligated organic structure. (see FIG. 8). On the return stroke of the knife 34, the shifter dog 130 moves back into locking engagement with the notch 128 of the knife 34 so that the main body portion 26 and the associated wrap 28 are also moved away from the anvil assembly 20 to open the jaws.

Figure 1:
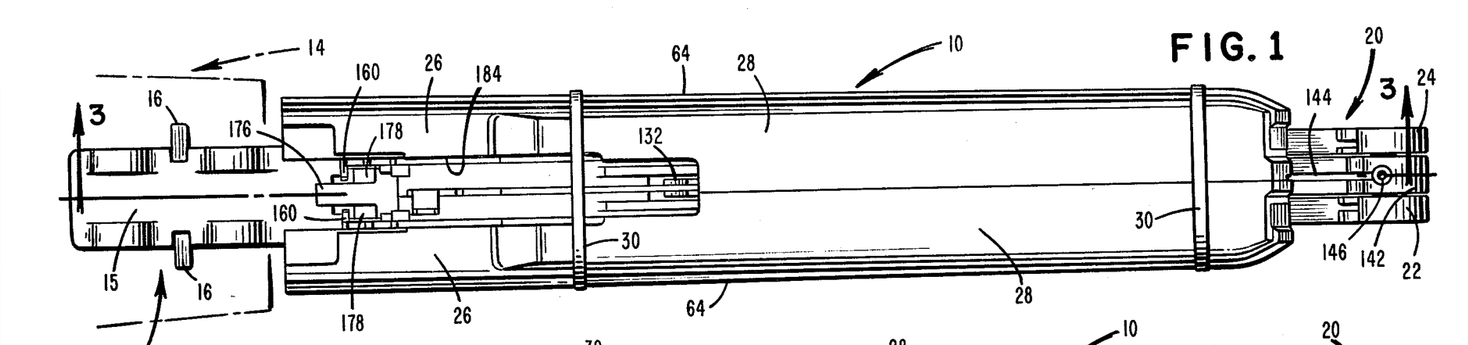
FIG. 1 is a top plan view of the cartridge.
Figure 5:
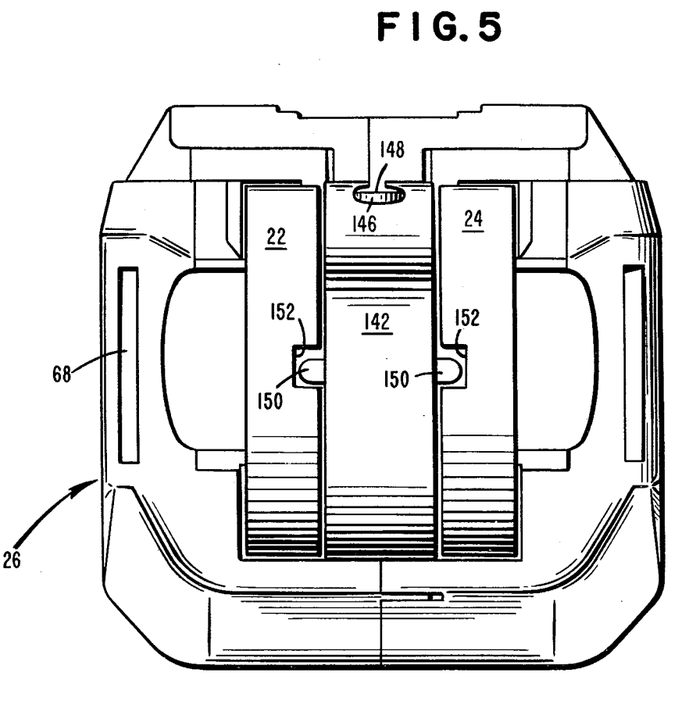
FIG. 5 is a front view of the cartridge.

With reference now particularly to FIGS. 1, 3 and 5, an ejector plate 140 is positioned between the forward ends of the rail assembly 12. The ejector plate 140 has an arcuate projection 142 at its forward end and a groove 144 extending longitudinally of the ejector plate for receiving the knife 34. The ejector plate is typically made of a rigid plastic material and has a soft plastic tube 146 which fits into a hole 148 extending from the top of the arcuate projection. The tube 146 is adapted to be cut into by the knife 34 when severing the organic structure. The arcuate projection has two outwardly and laterally extending ears 150 which slide in complimentary shaped slots 152 in the spaced apart anvils 22 and 24.

With reference now particularly to FIGS. 6–8, a downwardly extending lug 154 is formed on the bottom surface of the rear end of the ejector plate 140. The lug 154 extends through a longitudinally extending slot 156 formed in the anvil assembly 12. The slot 156 is made slightly longer than the length of the lug 154 thereby allowing slight relative movement between the ejector plate 140 and the anvil assembly 20.

A slot 158 is also formed in the bottom surface of the main body portions 26. The lug 154 of the ejector plate 140 extends through the slot 156 in the anvil assembly 12 into the slot 158 in the main body portions 26. The rear wall of the slot 158 in the main body portions abuts against the lug 154 of the ejector plate during its advance and causes the arcuate projection 142 to move forward away from the anvil assembly 20 as shown in FIGS. 7 and 8 so that the ears 150 on the arcuate projection are not within the jaws of the instrument as the organic structure is being enclosed and ligated. Then, on the return stroke of the main body portions 26, the ejector plate 140 is moved rearward into the position shown in FIGS. 1 and 2, for example, so that the ears 150 of the arcuate projection 142 engage the formed staples 80 to eject the staples and the severed organic structure from the jaws of the cartridge.

The main body portions 26 and associated wraps 28, the pushers 32, and the knife 34 are held in a fixed position relative to the rail assembly 12 until the cartridge 10 is mounted on the instrument 14. In this manner, the pushers 32 are prevented from accidentally ejecting a pair of staples 80 from the cartridge 10 and the knife 34 is prevented from accidentally travelling forward in the cartridge 10 before the cartridge is mounted on the instrument 14. Also, this arrangement properly positions the pushers 32 and the knife 34 to be engaged with the instrument.

Referring now particularly to FIGS. 1, 3 and 6–8, the pushers 32 are releasably locked, or held, with respect to the rail assembly 12 as follows as shown in FIGS. 1 and 3. On the inside surface of each of the pushers 12 at the rear end of the pushers, there is provided an ear 160. And, mounted in a slot 162 in the rear of the rail assembly 12 is a cartridge lock, or retaining member, 170 made of a resilient plastic material or the like. The cartridge lock 170 has a rounded pivot portion 172 which is supported by the lower surface of the main body portions 26. The forward end 174 of the cartridge lock is prevented from moving upward by the bottom surface of the wraps 28. The rear end of the cartridge lock 170 has an upstanding arcuate portion 176 and two outwardly and laterally projecting abutment surfaces 178. The rear end of the cartridge lock 170 is resiliently biased into the plane of the pushers 32 so that the abutment surfaces 178 are aligned with the ears 160 of the pushers when the cartridge is not associated with the instrument.

Therefore, when the pushers 32 are in their rearward-most position, with the cartridge ready to be inserted on the instrument 14, the abutment surfaces 178 of the cartridge lock 170 are positioned in front of the ears 160 and lock the pushers 32 in position with respect to the rail assembly 12 as shown in FIGS. 1 and 3. Also, when the pushers 32 are in this position, their rear ends are adjacent an abutment 180 on the main body portions 26 so that the main body portions 26 cannot move forward relative to the pushers 32. Finally, because of the engagement of the wraps 28 associated with the main body portions 26 and the knife 34 by means of the shifter dog 130, the knife is held in a fixed relative position with respect to the rail assembly 12. However, when the cartridge 10 is mounted on the instrument 14, as shown in FIGS. 6–8, the abutment surfaces 178 of the cartridge lock 170 are moved out of the plane of the ears 160 of the pushers 32 by means of the saddle 38 acting on the arcuate projection 176 and camming the rear end of the cartridge lock 170 downward into the slot 162 in the rail assembly 12. This unlocks the cartridge and allows the cartridge to be operated.

The operation of the inventive cartridge 10 is as follows. When the cartridge 10 is mounted on the instrument 14 as shown in FIGS. 6 and 10, the drive element 182 of the instrument extends through the opening 184 in the main body portions 26 so that the saddles 38 and 36 associate with the pushers 32 and knife 34, respectively. For this purpose, and as shown particularly in FIGS. 7 and 8, the pushers have a slot 186 and an inwardly extending flange 188 and the knife 34 has an upwardly and outwardly extending leg 190 defining an opening 192 at their respective rear ends.

Figure 2:
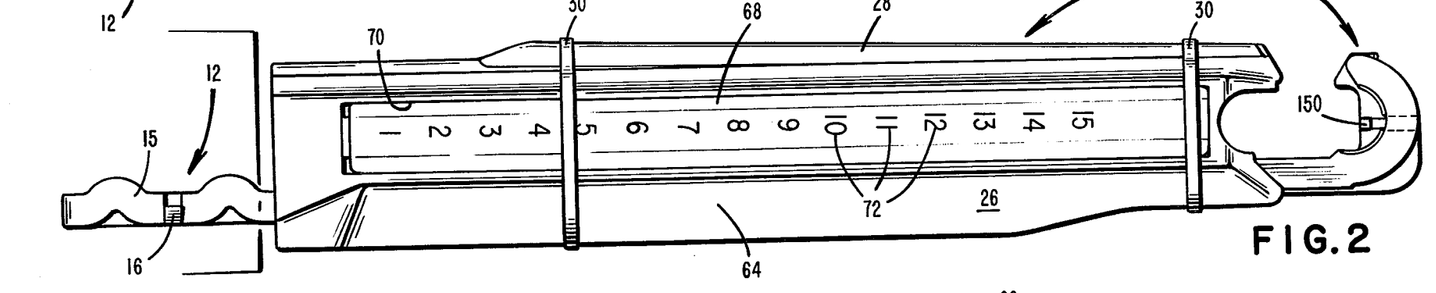
FIG. 2 is a side view of the cartridge.
Figure 13:
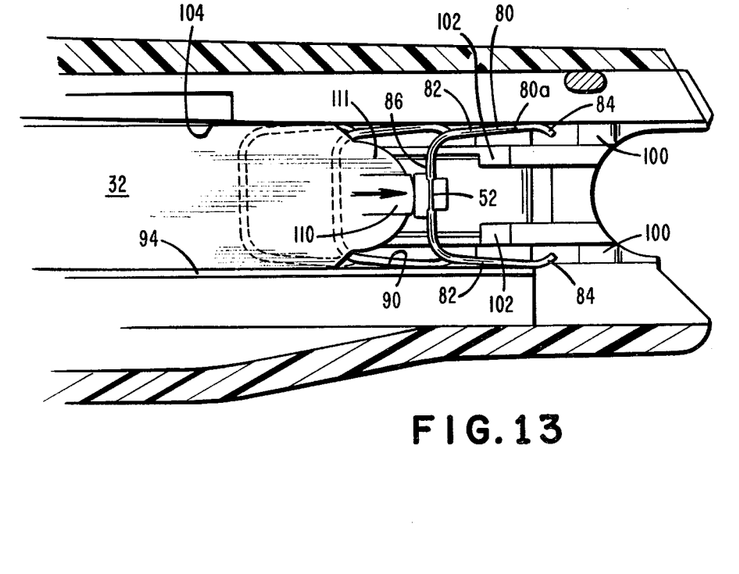
FIGS. 13 and 15 are enlarged views of the forward end of the cartridge as shown in FIG. 11 showing the advance of one of the pushers and one of the belts and the transfer of one of the forwardmost staples into the plane of the pusher in similar manner to FIGS. 12 and 14, respectively.

As noted previously, during shipment, the main body portions 26 and associated wraps 28 are retracted and spaced from the anvil assembly 20 as shown in FIGS. 1–3. Upon initial activation of the instrument 14, the knife 34 and therefore, by means of the shifter dog 130, the main body portions 26 and associated wraps 28 move in the direction of arrow 200. At the same time, the pushers 32 are moved forward and the teeth 110 of the pushers 32 come into contact as shown in FIGS. 12 and 13, with the rear surfaces of the teeth 50 of the belt 40 carrying the first staples 80 in the cartridge and move the belts 40 and associated staples 80 forward in unison with the main body portions 26 and associated wraps 28. During this movement, the staples remain in the index plane.

Figure 15:
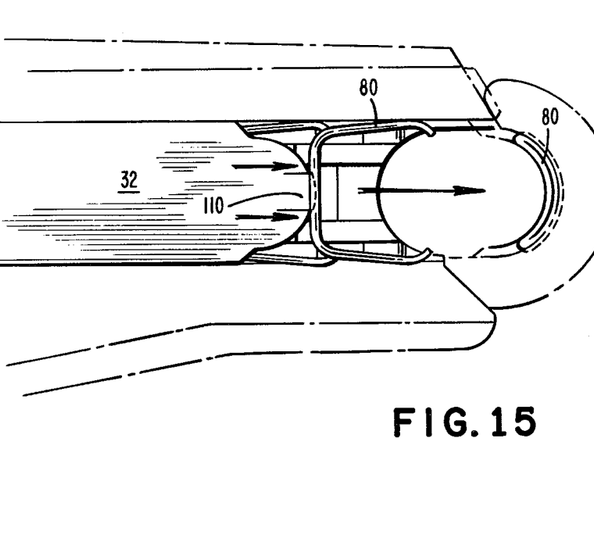

With continued movement of the belts 40, the arms 82 of the staples 80 come into contact with the ramps 100 and then the cross-pieces 86 of the staples 80 come into contact with the ramps 102. While the belts 40 are moving forward at this stage, the first staples 80 are held in the staple-carrying grooves 52 of the belts 40 by the leaf springs 118. The remaining staples 80 in the cartridge 10 are held in the staple-carrying grooves 52 of the belts 40 by the pushers 32 and the cover straps 98. With continued forward movement of the belts 40, and with the forward-most staples being acted upon by the respective ramps 100 and 102, the staples 80 are caused to transfer, in the direction of arrow 202, from the index planes to the pusher planes and cam the lips 114 of the springs 112 out of the pusher planes. The pushers 32 engage and also cam the leaf springs 118 out of the pusher planes (see FIGS. 14 and 15).

After the main body portions 26 and wraps 28 have come into contact with the anvil assembly 20 and ejector plate 140, respectively, as shown in FIG. 6, the upstanding arcuate portion 132 of the shifter dog 130 moves into the slot 138 in the anvil assembly 12 disengaging the wraps 28 from the knife 34. (See FIGS. 7 and 8). The pushers 32 continue their forward movement relative to the main body portions 26 and wraps 28 and contact the respective forwardmost staples 80, now moved into the pusher planes by the ramps 100 and 102, and form the same around the organic structure (not shown) housed within the jaws of the cartridge 10 as shown particularly in FIGS. 14 and 15 in similar manner to that shown in commonly assigned U.S. Pat. No. 3,683,927 the disclosure of which is expressly incorporated herein by reference. Then, once the organic structure is ligated, the knife 34 divides such structure intermediate the pair of ligating staples 80. (See FIG. 8).

Once a pair of staples 80 has been formed, and the organic structure has been divided, the knife 34, the pushers 32 and the main body portions 26 and associated wraps 28 are ready to be retracted from the region of the anvil assembly 20. First, the knife 34 retracts, then the pushers 32 retract and finally the main body portions 26 and associated wraps 28 retract once the upstanding arcuate portion 132 of the shifter dog 130 moves back into the notch 128 of the knife 34 during its return stroke. This sequence is opposite to that shown in FIGS. 6-8.

Before continuing, it should be noted that the forwardmost staples in the belts 40, save for the staples which were formed, were advanced by the belts 40 to a position immediately adjacent the ramps 100 and 102. The reference numeral 80a in FIG. 11 shows the position of the forwardmost staples in the main body portions 26, save for the staples having been ejected, after the completed movement of the belts 40 in the direction of arrow 200. These staples 80a, as well as the belts 40 and the remaining staples 80, are retained in this position by detents 60 which are positioned in the openings 54 between the forwardmost pairs of teeth 50. (See FIGS. 10 and 14).

The ejector plate 140 functions to eject the formed staples 80 and the severed organic structure from the jaws of the cartridge 10 after the completion of the ligating and dividing operations. During the forward motion of the main body portions 26, the ejector plate 140 is moved by the main body portions 26 out of the area of the anvil assembly 20 as shown in FIGS. 7 and 8. When the main body portions 26 retract, the ejector plate 140 is carried with the main body portions 26 into the area of the anvil assembly 20. (See FIGS. 1 and 3). In this manner, the inwardly extending ears 150 on the ejector plate 140 pass through the slots 152 in the pair of anvils 22 and 24 and force the staples 80 out of the area of the anvil assembly 20 and hence facilitate the ejection of the divided structure from the jaws of the cartridge 10.

As previously mentioned, the surgeon can ascertain the number of staples 80 in the cartridge 10 by reference to the indicia 72 on the cover plates 68 and the index marks 74 on the springs 48. However, if the surgeon fails to note that all of the staples 80 have been expelled from the cartridge and attempts to operate the instrument the cartridge is designed to prevent the forward stroke of the pushers and the knife. This also occurs should there be any malfunction of the cartridge such that a pair of staples is not in position to be formed. This is accomplished since the lips 114 of the springs 112, not being cammed out of the pusher planes by the staples moving up the ramps 100 and 102 and into the pusher planes, form abutments or stops for the pushers 32. In short, the lips 114 of the springs 112 remain in the position shown in FIG. 12 instead of being moved into the position shown in FIG. 14. Accordingly, although the jaws of the instrument may close around the organic structure, the pushers 32, acted upon by the lips 114 of the springs 112, cannot move forward. Because of the design of the instrument 14, the saddle 38 associated with the pushers 32 and therefore the saddle 36 associated with the knife 34 cannot move forward resulting in the knife 34 stopping in its forward movement before reaching and severing the organic structure.

Above there has been described a specific embodiment of the present invention. It should be noted, however, that the above description was given for illustrative purposes only and that many alterations and modifications may be practiced by those skilled in the art without departing from the spirit or the scope of the present invention. It is the intent therefore that the present invention not be limited to the above but be limited only as defined in the appended claims.

What is claimed is:

1. A cartridge adapted to be powered by a surgical instrument, said cartridge being capable of confining an organic structure in a closed area within the cartridge, ligating said structure with a pair of spaced apart surgical staples, and severing said structure intermediate said surgical staples, the cartridge comprising: a rail assembly adapted to be removably mounted to an instrument, said rail assembly having a forward end; anvil means defined at the forward end of said rail assembly; an elongate main body mounted on said rail assembly for movement longitudinally relative to said rail assembly; a pair of belts mounted in said main body for movement longitudinally relative to said main body, each belt defining an index plane; a plurality of surgical staples carried by said belts in said index plane; a pair of pushers each having a forward end mounted in said main body for movement longitudinally relative to said main body, each pusher mounted adjacent a respective belt of said pair of belts, each pusher defining a pusher plane, said pushers having a projection at each of their forward ends adapted to extend into the index plane of a respective adjacent belt for advancing said belts and said staples carried thereon toward said anvil means; ramp means associated with said main body and said belts for singly transferring said staples from the index planes and into the pusher planes in response to the movement of said pushers toward said anvil means; a knife mounted in said main body for longitudinal movement relative to said main body; and shifter means associated with said knife and said main body for causing said main body to move forward into abutting relationship with said anvil means, wherein a closed area defined by said anvil means and said main body when said knife is initially moved toward said anvil means is capable of confining an organic structure.

2. The cartridge of claim 1 in which each of said belts has a plurality of longitudinally spaced apart pairs of teeth on one side thereof, each pair of teeth defining a staple-carrying groove.

3. The cartridge of claim 2 in which said belts have a plurality of openings, each of said openings between two adjacent pairs of teeth, said cartridge further comprising a pair of detent means associated with said main body and aligned with said openings in said belts, said detent means being resiliently biased into the index planes defined by said belts to prevent said belts from moving away from said anvil means on the return stroke of said pushers.

4. The cartridge of claim 3 in which said detent means have sloped rear surfaces to permit said detent means to be cammed out of the index planes defined by said belts when said belts are being advanced toward said anvil means.

5. The cartridge of claim 1 and further comprising a cover plate associated with said main body having indicia thereon and a reference mark associated with said belt to permit the number of pairs of staples remaining in said cartridge to be ascertained.

6. The cartridge of claim 1 in which said staples have pairs of arms terminating in widely spaced apart ends which extend in the longitudinal direction of said main body toward said anvil means and cross-pieces which extend transversely of said arms and said belts, said cross-pieces of said staples being fitted into staple-carrying grooves of said belts.

7. The cartridge of claim 6 in which said arms of said staples, with the exception of the forwardmost staples in said cartridge, rest under the arms of the preceding staple in "shingle" fashion.

8. The cartridge of claim 6 in which said ramp means for transferring said staples from the index planes defined by said belts into the pusher planes of said pushers comprise a series of ramps which act upon said arms and said cross-pieces of said staples.

9. The cartridge of claim 8 in which said ejector means has a rear end with a bottom surface and a downwardly extending lug formed on the bottom surface of the rear end of said ejector means, said rail assembly having a longitudinally extending slot through which said lug extends, said longitudinally extending slot being slightly longer than the length of said downwardly projecting lug to allow for slight relative movement between said ejector means and said anvil means.

10. The cartridge of claim 9 in which said ejector means is moved relative to said anvil means by means of association of said lug with said main body.

11. The cartridge of claim 1 in which the rear surfaces of said projections at the forward ends of said pushers are sloped to allow said pushers to be cammed out of the index planes defined by said belts during the return strokes of said pushers.

12. The cartridge of claim 1 in which the forward ends of said pushers are curved and are adapted to be cooperate with said staples during the ligating operation.

13. The cartridge of claim 1 in which said main body includes a pair of spaced apart wraps each having a forward end adjacent a respective pusher and a spring associated with each of said wraps near their forward ends.

14. The cartridge of claim 13 in which said springs have lips which are resiliently biased into the pusher planes of said pushers and are adapted to be cammed out of the pusher planes of said pushers by the forwardmost staples, said lips acting to prevent the forward movement of said pushers when a pair of staples is not in position in the pusher planes of said pushers ready to be formed in the ligating operation.

15. The cartridge of claim 13 in which said springs also include leaf springs which project into the index planes defined by said belts and are positioned to hold the forwardmost staples in said belts until said staples are ready to be transferred from the index planes defined by said belts into the planes of said pushers.

16. The cartridge of claim 1 in which said shifter means includes means hingedly attached to said main body at one end and an upstanding arcuate portion at its other end, said knife further comprising a notch adapted to associate with said upstanding arcuate portion during the initial movement of said knife toward said anvil means and during the final stages of the movement of said knife away from said anvil means when said knife is being returned to its initial rest position.

17. The cartridge of claim 16 in which said rail assembly has a longitudinally extending opening which is adapted to receive the rear end of said upstanding arcuate portion on said shifter means to allow said shifter means to be moved out of engagement with said notch in said knife after the jaws of said instrument have been closed.

18. The cartridge of claim 1 and further comprising ejector means for ejecting said staples and said organic structure from the jaws of said cartridge after the ligating and severing operations.

19. The cartridge of claim 18 in which the forward end of said rail assembly is formed into two spaced apart sections defining spaced apart anvils at their forward ends and said ejector means is positioned between said spaced apart sections of said rail assembly.

20. The cartridge of claim 19 in which said ejector means has a foreward end and an arcuate projection at its forward end and a groove extending, longitudinally of said ejector means for receiving said knife.

21. The cartridge of claim 20 in which said ejector means has two outwardly and laterally extending ears defined by said arcuate projection which slide in complimentary shaped slots in said spaced apart anvils.

22. The cartridge of claim 1 and further comprising means for releasably holding said main body, said pushers and said knife in a fixed position relative to said rail assembly.

23. The cartridge of claim 22 in which said means for releasably holding comprises a cartridge retaining member which is resiliently urged into abutment with said pushers to prevent said pushers from moving toward said anvil means.

24. The cartridge of claim 23 in which said cartridge retaining member has a round pivot portion which is supported by the upper surface of said main body and the rear end of said cartridge retaining member has an upstanding arcuate portion and two outwardly and laterally projecting abutment surfaces, said rear end of said cartridge retaining member being resiliently biased into the pusher planes of said pushers so that said abutment surfaces are aligned with and in front of ears mounted on said pushers.

25. The cartridge of claim 24 in which said cartridge retaining member is mounted on said cartridge such that it is adapted to be moved out of abutment with said pushers.

26. A cartridge adapted to be powered by a surgical instrument, said cartridge being capable of confining an organic structure in a closed area within the cartridge, ligating said structure with a pair of spaced apart surgical staples, and severing said structure intermediate said surgical staples, the cartridge comprising: a rail assembly adapted to be removably mounted to an instrument, said rail assembly having a forward end; anvil means defined at the forward end of said rail assembly; an elongate main body mounted on said rail assembly for movement longitudinally relative to said rail assembly; staple feeding means defining a pair of index planes mounted in said main body for movement with said main body; a plurality of surgical staples fed by said staple feeding means; a pair of pushers, each defining a pusher plane, mounted in said main body for movement longitudinally relative to said main body adjacent said respective staple feeding means for singly transferring said staples from the index planes defined by said staple feeding means and into the pusher planes of said pushers; a knife mounted in said main body for longitudinal movement relative to said main body; and shifter means associated with said knife and said main body for causing said main body to move forward into abutting relationship with said anvil means, wherein a closed area defined by said anvil means and said main body when said knife is initially moved toward said anvil means is capable of confining an organic structure.

27. A cartridge adapted to be powered by a surgical instrument, said cartridge being capable of confining an organic structure in a closed area within the cartridge, ligating said structure with a pair of spaced apart surgical staples, and severing said structure intermediate said surgical staples, the cartridge comprising: a rail assembly adapted to be removably mounted to an instrument, said rail assembly having a forward end; anvil means defined at the forward end of said rail assembly; an elongate main body mounted on said rail assembly for movement longitudinally relative to said rail assembly; a pair of belts, each defining an index plane, mounted in said main body for movement longitudinally relative to said main body; a plurality of surgical staples carried by said belts; a pair of pushers, each defining a pusher plane, mounted in said main body for movement longitudinally relative to said main body adjacent said respective belts, said pushers having a projection at each of their forward ends adapted to extend into the index plane defined by a respective belt for advancing said belts and said staples carried thereon toward said anvil means; ramp means associated with said main body and said belts for singly transferring said staples from the index planes defined by said belts and into the pusher planes of said pushers in response to the movement of said pushers toward said anvil means; and a knife mounted in said main body for longitudinal movement relative to said main body.

28. A cartridge adapted to be powered by a surgical instrument, said cartridge being capable of confining an organic structure in a closed area within the cartridge and ligating said structure with a surgical staple, the cartridge comprising: a rail assembly adapted to be removably mounted to an instrument, said rail assembly having a forward end; anvil means defined at the forward end of said rail assembly; an elongate main body mounted on said rail assembly for movement longitudinally relative to said rail assembly; a belt mounted in said main body for movement longitudinally relative to said main body, said belt defining an index plane; a plurality of surgical staples carried by said belt in said index plane; a pusher, defining a pusher plane, mounted in said main body for movement longitudinally relative to said main body adjacent said belt, said pusher having a projection at its forward end adapted to extend into the index plane defined by said belt for advancing said belt and said staples carried thereon toward said anvil means; and ramp means associated with said main body and said belt for singly transferring said staples from the index plane defined by said belt and into the pusher plane of said pusher in response to the movement of said pusher toward said anvil means.

* * * * *